United States Patent [19]

Hubertus van Veen

[11] Patent Number: Plant 5,477

[45] Date of Patent: May 28, 1985

[54] CHRYSANTHEMUM

[75] Inventor: Johannes W. Hubertus van Veen, Ter Aar, Netherlands

[73] Assignee: Chrysanthemum Breeders Assoc. N.V., Curacao, Netherlands Antilles

[21] Appl. No.: 517,219

[22] Filed: Jul. 25, 1983

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Thomas E. Schatzel

[57] ABSTRACT

A vigorous chrysanthemum plant bearing white blossoms having a daisy-anemone form.

3 Drawing Figures

BACKGROUND OF THE NEW PLANT

The present invention comprises a new and distinct cultivar of chrysanthemum plant which is a cross of unknown parents. The new cultivar has the commercial name of Refour, was discovered by Johannes Wensalaus Hubertus van Veen in September, 1978, at revecu b.v. paradysweg 88, 2461tp Ter Aar, in the Netherlands, and has been asexually reproduced by cuttings at the same location. The new cultivar has been found to retain its distinctive characteristics through successive propagations.

DESCRIPTION OF THE DRAWING

The accompanying drawings show the unique characteristics of the new cultivar, the color being as nearly true as possible with color illustrations of this type.

DESCRIPTION OF THE NEW PLANT

Figure 1:
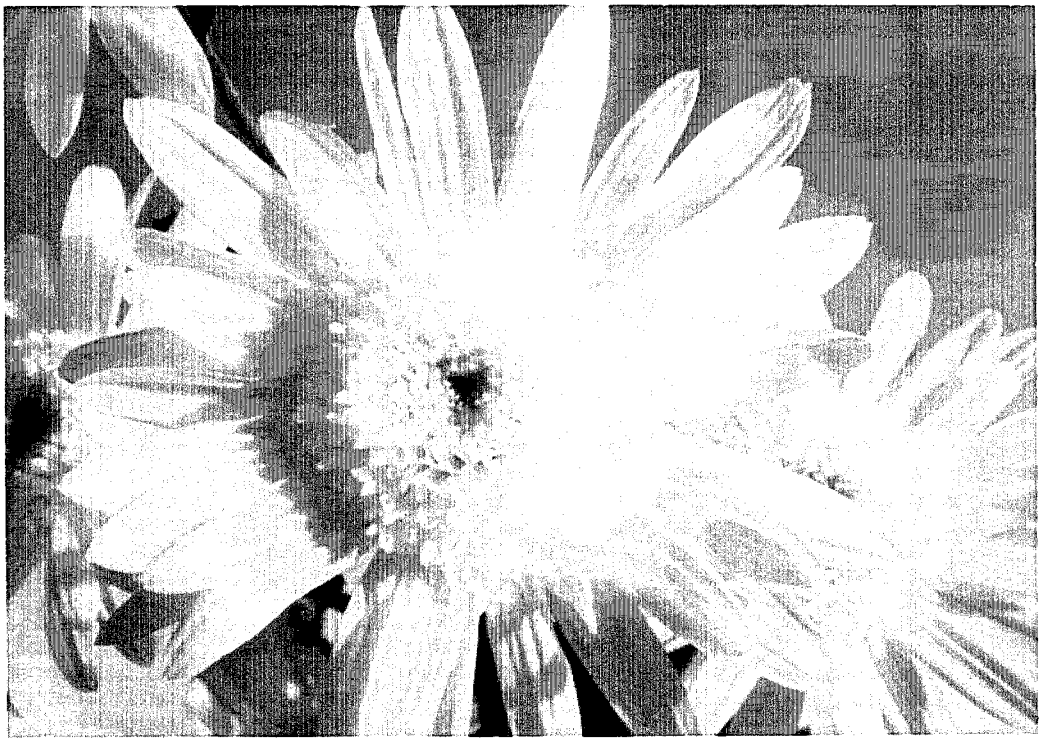
FIG. 1 shows the new cultivar in full bloom.
Figure 3:
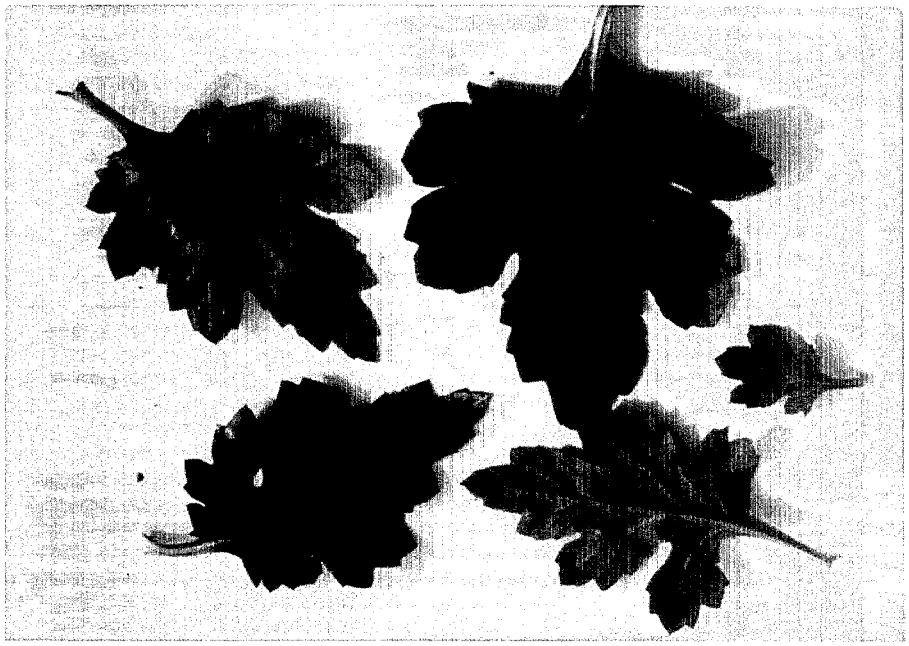
FIG. 3 shows foliage of the new cultivar.
Figure 2:
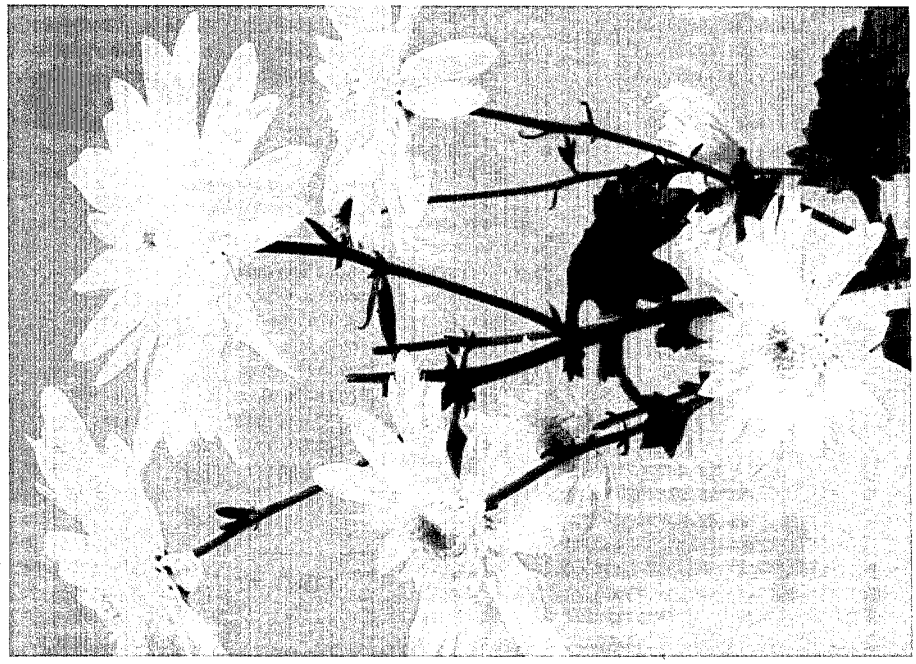
FIG. 2 shows the new cultivar in various stages of bloom.

The new cultivar is a short day response plant and, when grown in the vicinity of Beverlanderhof, Ter Aar, Holland, has a response time of about eight and one-half weeks. The new cultivar has been found to retain its distinctive characteristics through successive propagations and may be grown year round under greenhouse conditions.

In the description which follows, color references are made to the "Horticultural Colour Chart I & II" issued by the British Colour Council in collaboration with The Royal Horticultural Society, Copyright Robert F. Wilson, Vol. I, 1938; Vol. II, 1941, printed by Henry Stone and Son, Ltd., Banbury, England.

Bud:
- *Size.*—Medium.
- *Form.*—Flat top, short form; unaffected by wet-hot weather.
- *Color.*—When sepal first devide, 155d. When sepal begins to unfurl 155d. When half bloom inside of petals 155d and reverse of petals 155d.

Botanical classification: *Chrysanthemum morifolium.*

Bloom:
- *Size.*—Medium.
- *Fully expanded.*—8–9 Centimeters.
- *Borne.*—Single, sometimes several per peduncle.
- *Stems.*—Medium, strong.

- *Form.*—Single, (daisy), short with a flat top, unaffected by wet-hot weather, when first open is cripped, anemone type.
- *Permanence.*—Excellent, 4 weeks.

Color:
- *Center of flower.*—155d.
- *Base of petals.*—155d.
- *Inside of petals.*—155d.
- *Reverse of petals.*—155d.
- *Outer petals.*—155d.
- *Tonality from a distance.*—The flower is pure white and depending on the growing conditions, has a green to light yellow tone to the center, which disappears in a later stage.
- *Discoloration.*—After 3 weeks 155d to tints of red-purple 72b.

Petals:
- *Texture.*—Two rows.
- *Number.*—Normally 24–26.
- *Arrangement.*—Imbricated.
- *Persistence.*—Petals hand-down and dry.
- *Fragrance.*—Typical chrysanthemum.

Reproductive organs:
- *Stamen.*—Few, small.
- *Pollen.*—None.
- *Styles.*—Columnar.
- *Length.*—Short, thin.
- *Stigmas.*—Dresden Yellow 64.
- *Ovaries.*—Enclosed in calyx.

Plant:
- *Form.*—Herbaceous.
- *Growth.*—Vigorous.
- *Height.*—Medium to tall, depending on culture.
- *Peduncle.*—Strong.

Foliage:
- *Color.*—Upperside yellow green 147a. Underside yellow green 147b.
- *Size.*—Short to medium.
- *Quantity.*—Normal.
- *Shape.*—Pointed oval.
- *Texture.*—Upperside leathery, medium thick, underside smooth to heavy.
- *Ribs and veins.*—Ordinary.
- *Edge.*—Undulated.
- *Leaf underside.*—Smooth to heavy.

I claim:

1. A new and distinct cultivar of chrysanthemum, substantially as described and pictured herein, characterized by its pure white blooms, vigorous growth, eight and one-half week response and permanence.

* * * * *